United States Patent [19]

Bauer

[11] Patent Number: 5,593,421
[45] Date of Patent: Jan. 14, 1997

[54] SUTURE ELEMENT DELIVERY DEVICE AND METHOD

[76] Inventor: William Bauer, Newnan Medical Plaza, Suite 204, 58 Hospital Rd., Newnan, Ga. 30263

[21] Appl. No.: 467,139

[22] Filed: Jun. 6, 1995

[51] Int. Cl.$^6$ .................................................. A61B 17/00
[52] U.S. Cl. ........................ 606/213; 606/139; 606/220; 227/901
[58] Field of Search .................................. 606/139, 144, 606/145, 148, 151, 143, 142, 213, 215, 216, 218, 219, 220; 227/175.1, 176.1, 177.1, 178.1, 179.1, 181.1, 19, 901; 112/169, 80.03

[56] References Cited

U.S. PATENT DOCUMENTS

| 4,532,926 | 8/1985 | O'Holla | 606/220 |
|---|---|---|---|
| 4,784,137 | 11/1988 | Kulik et al. . | |
| 5,040,715 | 8/1991 | Green et al. . | |
| 5,125,553 | 6/1992 | Oddsen et al. . | |
| 5,282,811 | 1/1994 | Booker et al. | 606/157 |
| 5,423,471 | 6/1995 | Mastri et al. | 227/175.1 |
| 5,423,858 | 6/1995 | Bolanos et al. | 606/220 |
| 5,470,338 | 11/1995 | Whitfield et al. | 606/148 |

Primary Examiner—Michael Powell Buiz
Assistant Examiner—Jeffrey A. Schmidt
Attorney, Agent, or Firm—Cushman Darby & Cushman IP Group Pillsbury Madison & Sutro, LLP

[57] ABSTRACT

An endoscopic, suture element delivery device is provided including an elongated arm assembly having proximal and distal ends. A series of successive suture elements and a series of successive receptacle elements are carried by the arm assembly. A suture delivery structure is mounted with respect to the housing assembly for movement between a retracted position disposed within the housing assembly and an extended position extending from the housing assembly. The suture delivery structure is constructed and arranged to engage a forwardmost suture element. A receptacle delivery structure is mounted to a distal end of the housing assembly and is movable between receptacle loading and unloading positions. The receptacle delivery structure is constructed and arranged to engage a forwardmost receptacle element. An actuating structure is carried by the arm assembly and is constructed and arranged to move the suture delivery structure between its retracted and extended positions and the receptacle delivery structure between its loading and unloading positions. A handle structure is coupled to the proximal end of the arm assembly and is operatively coupled to the actuating structure for moving the actuating structure.

18 Claims, 16 Drawing Sheets

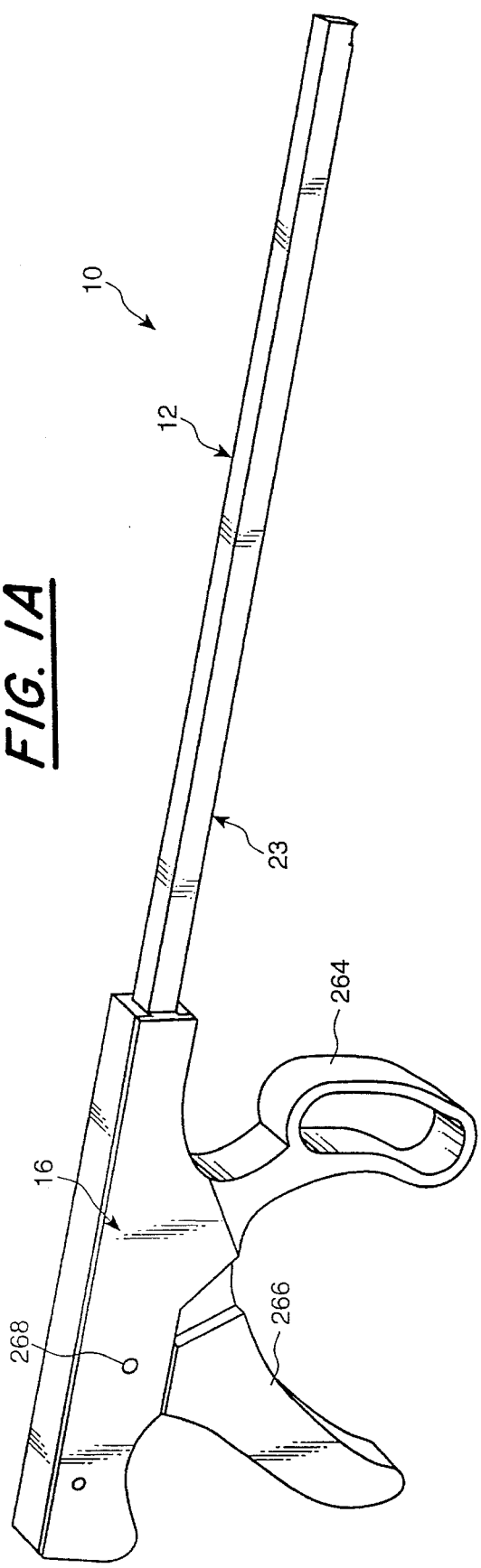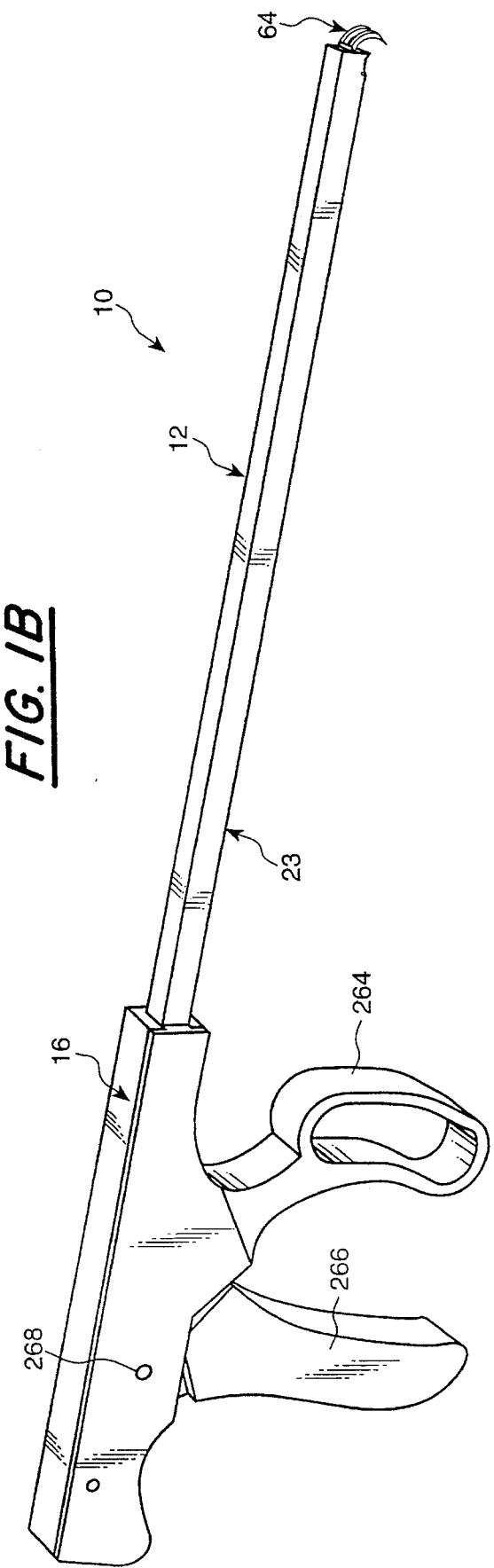

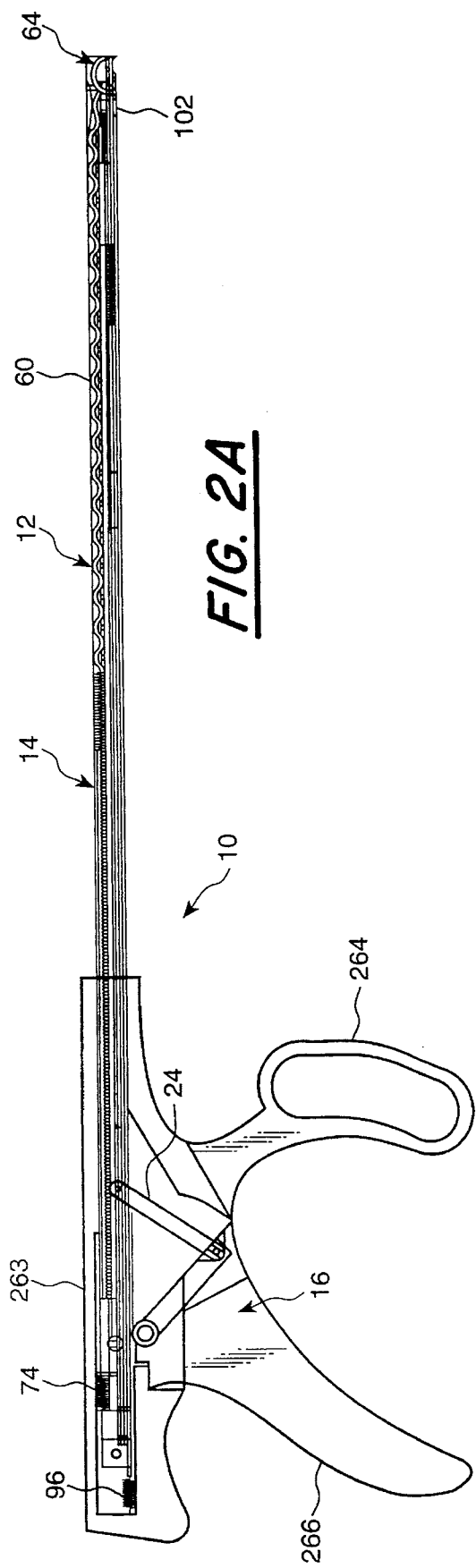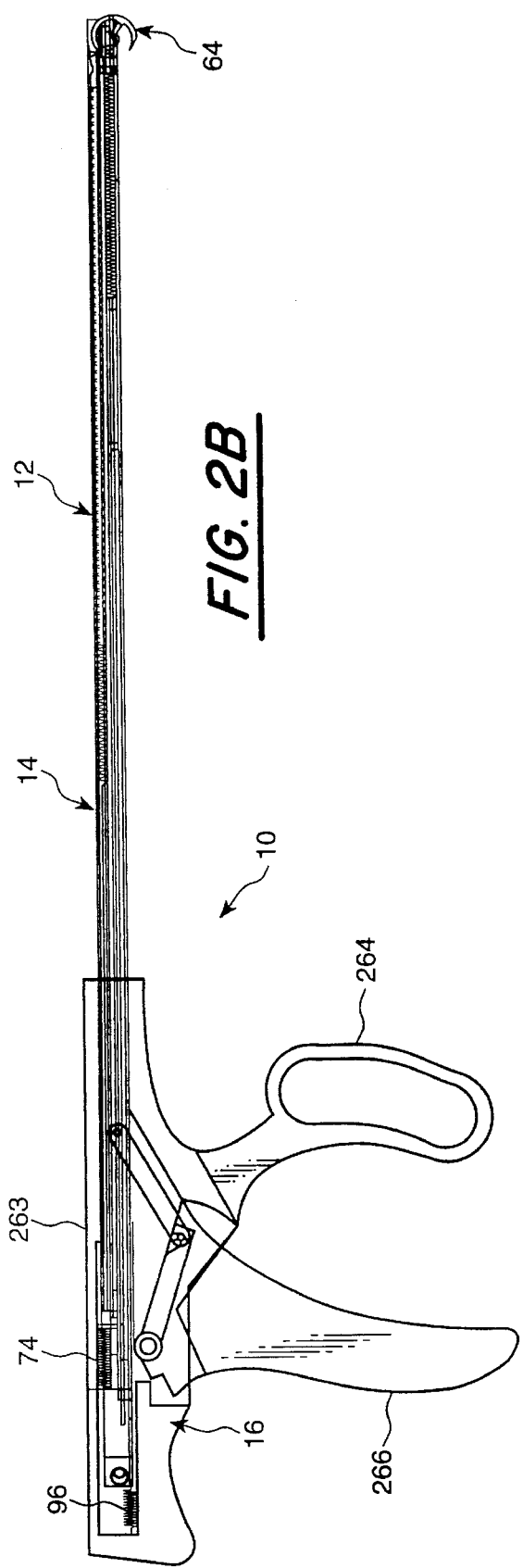

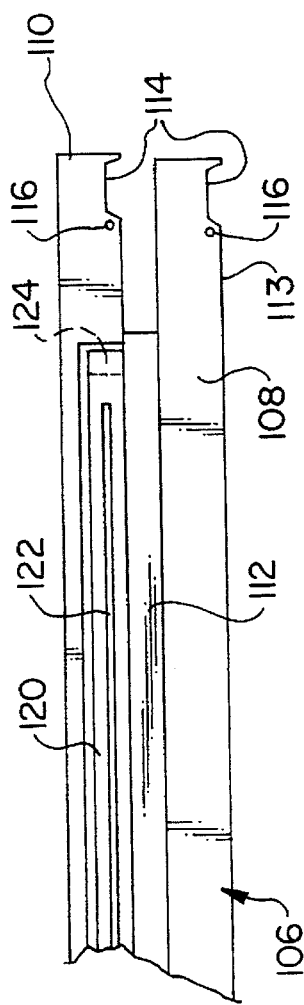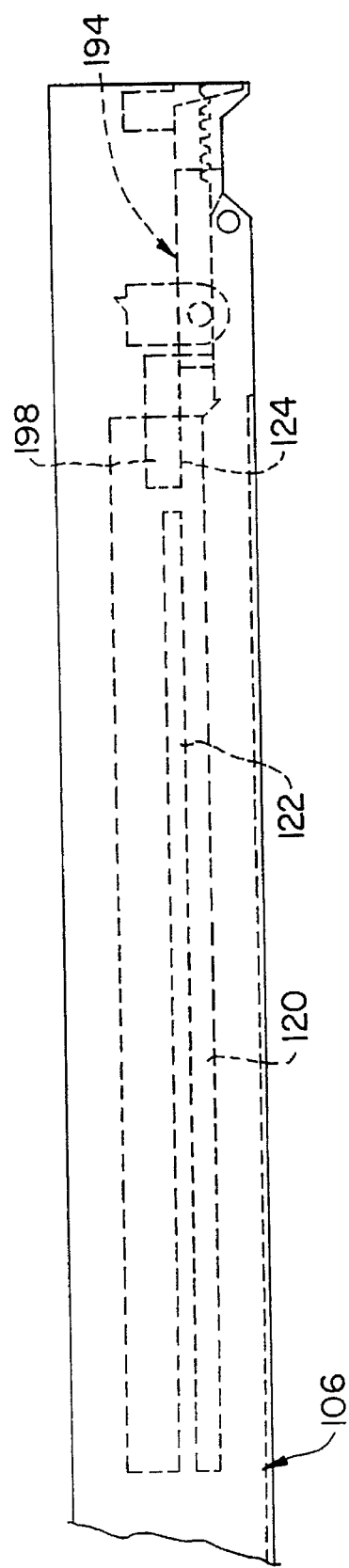
FIG. 21
FIG. 22

SUTURE ELEMENT DELIVERY DEVICE AND METHOD

BACKGROUND OF THE INVENTION

This invention relates to a device for suturing tissue, and, more particularly, to a suture element delivery device for delivering suture elements endoscopically.

Endoscopic suturing is a technique that is presently in its early evolutionary state. Endoscopic surgery has gained acceptance and is proven to justify itself with minimum surgical invasion and cost effective reduction in hospitalization and recovery time. Visualization with endoscopes, manipulation of tissue with micro-instruments, and control of bleeding with electrocautery and lasers are all highly developed. However, an area that has yet to be fully developed is suturing endoscopically.

Various methods have been developed to suture or fasten tissue at a distance. These methods include clipping or utilizing a device that passes a needle and suture through the tissue. However, these methods are cumbersome and at times difficult to perform.

SUMMARY OF THE INVENTION

An object of the present invention is to provide a device for delivering a suture element endoscopically. The device can be used with conventional 10 mm trocars which are commonly employed in laparoscopic surgery. In accordance with the principles of the present invention, this and other objectives are achieved by providing a suture element delivery device including an elongated arm assembly including a housing having proximal and distal ends. A series of successive suture elements and a series of successive receptacle elements are carried by the arm assembly.

A suture delivery structure is mounted to the housing assembly for movement between a retracted position disposed within the housing assembly and an extended position extending from the housing assembly. The suture delivery structure is constructed and arranged to engage and displace a forwardmost suture element. A receptacle delivery structure is mounted to a distal end of the housing assembly and is movable between receptacle loading and unloading positions. The receptacle delivery structure is constructed and arranged to engage and displace a forwardmost receptacle element.

An actuating structure is carried by the arm assembly and is constructed and arranged to move the suture delivery structure between its retracted and extended positions and the receptacle delivery structure between its loading and unloading positions.

A handle structure is coupled to the proximal end of the arm assembly and is operatively coupled to the actuating structure. The handle structure is movable between first and second positions such that movement of the handle structure from its first position to its second position during a suturing operation moves the actuating structure between first and second positions, thereby moving the suture delivery structure from its retracted position to its extended position and moving the receptacle delivery structure from its loading position to its unloading position such that a forwardmost suture element and an associated forwardmost receptacle element are moved from the distal end of the housing assembly with the suture element engaging the receptacle element.

Movement of the handle structure from its second position to its first position returns the actuating structure to its first position and moves the suture delivery structure from its extended position to its retracted position and moves the receptacle delivery structure from its unloading position to its loading position. The device can be used with conventional 10 mm trocars which are commonly employed in laparoscopic surgery.

In accordance with yet another aspect of the present invention, a method of delivering a suture element endoscopically with a suture element delivery device, of the type described above, is provided. The method includes moving the device such that the arm assembly thereof is disposed at a suture delivery location. The handle structure is then moved from its first position to its second position during a suturing operation thereby moving the actuating structure between first and second positions so as to move the suture delivery structure from its retracted position to its extended position and move the receptacle delivery structure from its loading position to its unloading position. These movements cause a forwardmost suture element and an associated forwardmost receptacle element to be moved from the distal end of the housing assembly into tissue with the suture element engaging the receptacle element.

Releasing the handle structure from its second position so as to return the actuating structure to its first position moves the suture delivery structure from its extended position to its retracted position and moves the receptacle delivery structure from its unloading position to its loading position.

Other objects, features and characteristics of the present invention, as well as the function of the related elements of the structure, and the combination of parts and economies of manufacture, will become more apparent upon consideration of the following detailed description and the appended claims with reference to the accompanying drawings, all of which form a part of this specification.

BRIEF DESCRIPTION OF THE DRAWINGS

FIG. 1A is a perspective view of an endoscopic suture element delivery device provided in accordance with the principles of the present invention, in a first, unactuated position;

FIG. 1B is a perspective view of the device of FIG. 1A, in a second, actuated position;

FIG. 2A is a schematic, front view of the device of FIG. 1A, with some parts omitted for clarity of illustration;

FIG. 2B is a schematic front view of the device shown in FIG. 1B, with some parts omitted for clarity of illustration;

FIG. 21 is an enlarged, perspective view of the distal portion of the lower housing portion of the arm assembly;

FIG. 22 is a partial, side elevational view showing the brace structure fixed to a distal end of the lower housing portion of the arm assembly;

DETAILED DESCRIPTION OF THE PRESENTLY PREFERRED EXEMPLARY EMBODIMENT

Figure 3B:
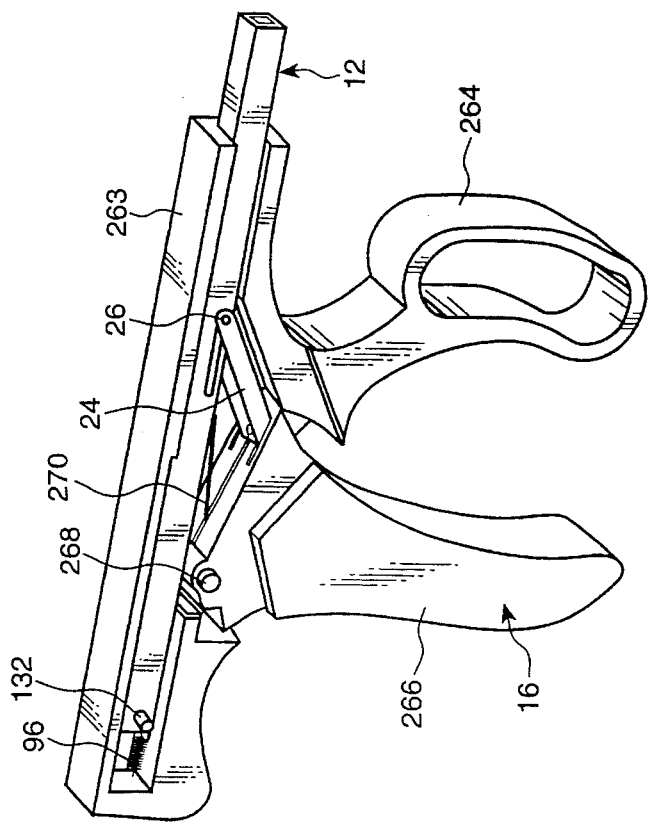
FIG. 3B is a view similar to FIG. 3A, with the handle structure in its second, actuated position.

Referring to the drawings, an endoscopic suture element delivery device is shown, generally indicated at 10, which embodies the principles of the present invention.

The delivery device 10 includes an elongated arm assembly, generally indicated at 12, including actuating structure, generally indicated at 14. Suture delivery structure 64 and receptacle delivery structure 118 are carried by the arm assembly 12 and cooperate with the actuating structure 14. Handle structure 16 is coupled to the actuating structure 14 and movable between first and second positions such that movement of the handle structure 16 from its first position to its second position moves the actuating structure 14 thereby moving the suture and receptacle delivery structure, as will become apparent below.

Figure 4:
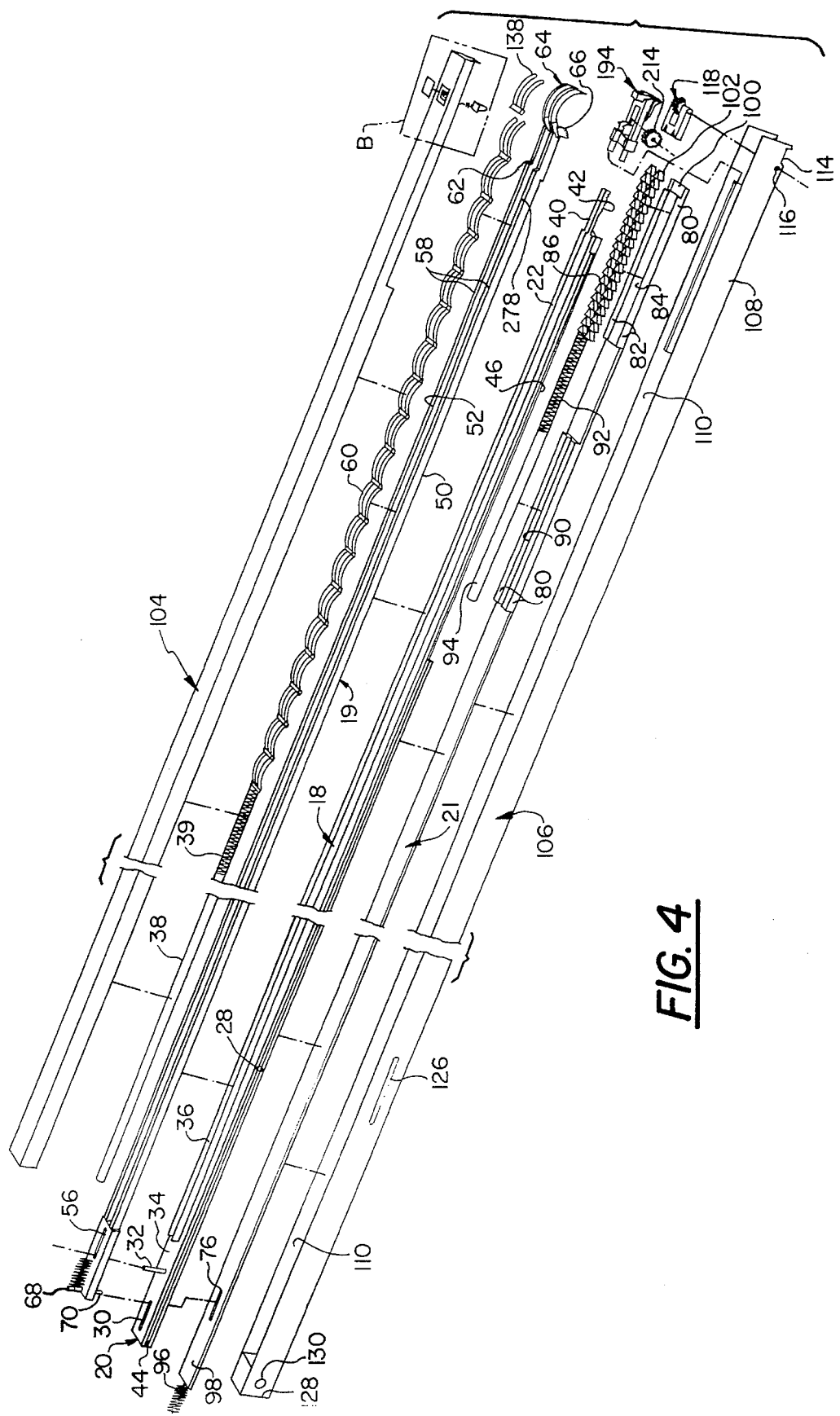
FIG. 4 is an exploded view of the arm assembly of the delivery device of the present invention.

With reference to FIG. 4, the elongated arm assembly 12 carries a first slide member 18, a second slide member 19, and a third slide member 21 within a housing assembly 23.

The first slide member 18 has a proximal portion 20 and a distal portion 22. The proximal portion 20 is connected to the handle structure 16 via lever arms 24 (FIG. 3A) which are disposed on opposing sides of the first slide member 18 and coupled to the first slide member 18 via pins 28, which are received in bores 26 of the lever arms 24. Thus, the first slide member 18 is movable between first and second positions upon movement of the handle structure 16 between its first and second positions. The proximal portion 20 further includes a slot 30 extending in a longitudinal direction of the first slide member 18 and an upstanding pin 32 extending from an upper surface 34 of the first slide member 18. As shown in FIG. 4, a channel member 36 is provided on surface 34 of the first slide member 18. The channel member 36 defines a channel in which a suture spring bar 38 is slidably disposed. The spring bar 38 and spring 39 assembly defines biasing structure of the arm assembly 12, for biasing suture elements towards a distal end of the arm assembly 12. The channel member 36 includes a surface defining a stop (not shown in detail) near a central portion thereof which provides a backstop for the spring 39 which biases the suture spring bar 38 towards the distal end of the arm assembly 12. Other suitable spring biasing or incremental advancement mechanisms are known and could be incorporated in the device in lieu of or as a supplement to the spring 39 and bar 38 assembly shown.

The distal portion 22 of the first slide member 18 includes an elongate or flat gear 40 having a plurality of teeth 42, as will be explained in further detail below.

Figure 5:
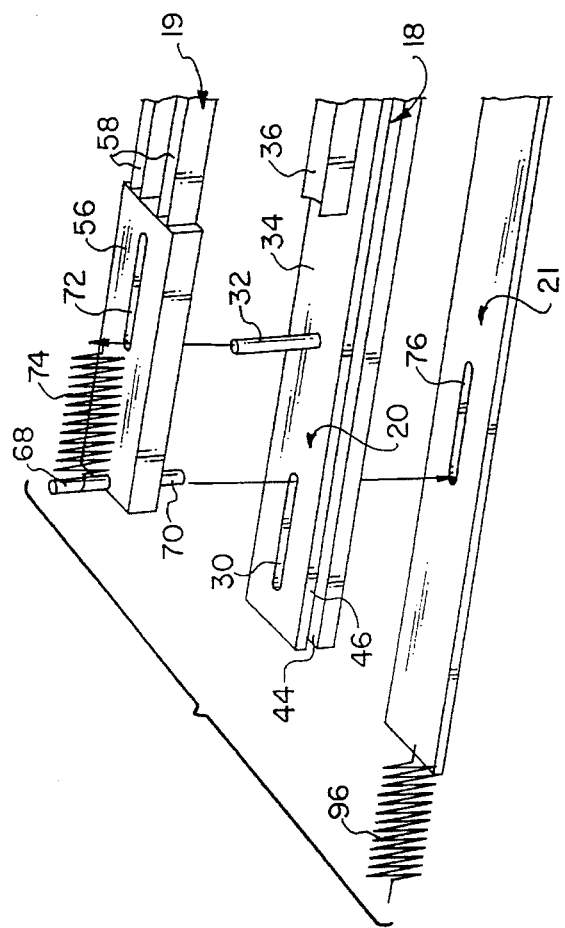
FIG. 5 is an enlarged, partial exploded view of proximal end portions of the first, second, and third slide members of the arm assembly of FIG. 4.

As shown in FIGS. 4 and 5, the first slide member 18 includes a groove 44 defined in each side wall thereof. The groove 44 defines a ledge 46 which extends the length of the first slide member 18. The ledge 46 engages the housing assembly 23 so that the slide member 18 will slide axially or longitudinally of the housing assembly 23 when displaced by the handle structure.

The second slide member 19 consists of a pair of longitudinal arms 50 and 52 joined at their proximal ends by a flat plate 56. As best shown in FIG. 5, grooves or channels 58 extend along the top of each arm 50, 52 to permit suture elements 60 to slide along the length of the arms 50 and 52. The distal end 62 of each arm 50, 52 includes a step which allows a suture element to drop to an appropriate position to be loaded into the suture delivery structure, in the form of a suture needle 64, which is pivotally coupled to the distal end of the pair of arms via axle 66. The flat plate 56 includes two pegs 68 and 70. The peg 68 extends upwardly from the plate 56 and is connected via a spring 74 to pin 32 of the first slide member 18 which extends through slot 72 in the flat plate 56. Peg 70 extends downwardly from an underside of the plate 56 through slot 30 of the first slide member 18 and into slot 76 defined in the third slide member 21.

Figure 3A:
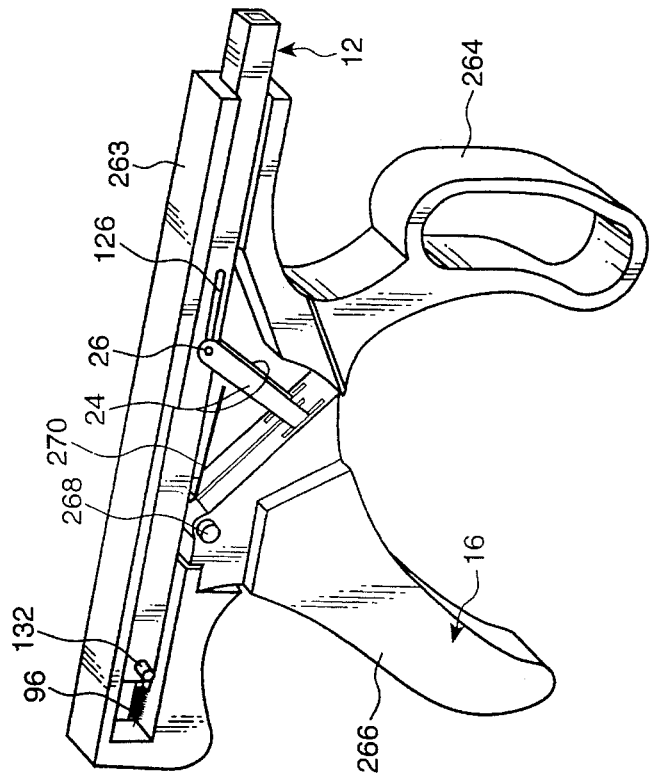
FIG. 3A is a partial, perspective view of the handle structure of the device of FIG. 1A.

The distal end 80 of the third slide member 21 includes a pair of elevations 82 defining a groove 84 therebetween, which serves to hold receptacle elements 86 in place. Just proximal to the elevation 82 is another pair of elevations 88 defining a second groove 90 therebetween which serves as a backstop for a spring 92 coupled to receptacle bar 94. The spring/bar assembly defines biasing structure of the arm assembly 12, for biasing the series of receptacle elements towards the distal end of the arm assembly 12. A spring 96 couples the proximal end 98 of the third slide member 21 to the handle structure 16, as shown in FIG. 3A. The bias of the spring 96 returns the third slide member 21 to its first or initial position, as will become apparent below. The distal end 80 of the third slide member 21 includes a stepped portion 100 allowing a forwardmost receptacle element 102 to drop to a lower level separating it from the series of receptacle elements 86, as will be explained in greater detail below.

As noted above, the arm assembly 12 includes a housing assembly 23 having an upper housing portion 104 and a lower housing portion 106 (FIG. 4). In the illustrated embodiment, the lower housing portion 106 consists of two longitudinal side walls 108 and 110 and a bottom surface 112 (FIG. 21). The distal end 113 of the lower housing portion 106 includes notches 114 in side walls thereof which receives tissue to be sutured during the suturing process. Directly behind the notches 114 are openings 116 which serve to couple the receptacle delivery structure, in the form of a receptacle arm, generally indicated at 118, thereto. As best shown in FIG. 21, each side wall 110, 112 includes reliefs 120 defining slots 122, which cooperate with the ledges 46 of the first slide member 18 such that the first slide member 18 is slidable with respect to the housing assembly 23. In addition, a notch 124 is defined in the end of each relief 120 for receiving brace structure 194, as will be explained below. As shown in FIG. 4, the side walls 110 and 112 each contain a slot 126 therein which receives pin 28 of the first slide member 18, when the first slide member moves with respect to the stationary lower housing portion 106. The proximal portion 128 of the lower housing portion 106 is solid with a bore 130 disposed therethrough. A pin 132 is disposed through the bore 130 coupling the lower housing portion 106 to the handle structure 16.

Figure 9:
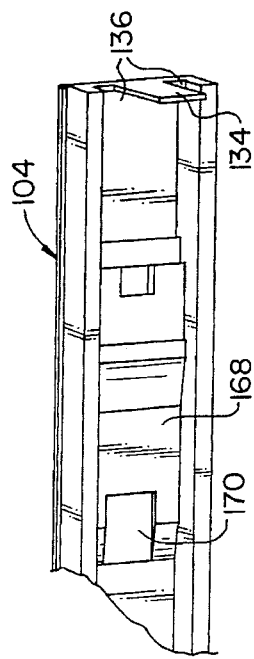
FIG. 9 is an enlarged, perspective view of portion A of FIG. 8.
Figure 8:
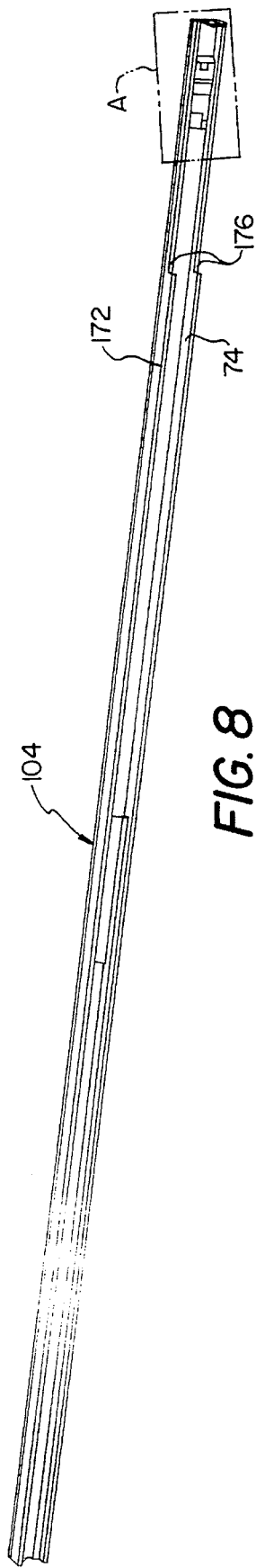
FIG. 8 is a perspective view of the top housing portion of the arm assembly.
Figure 18:
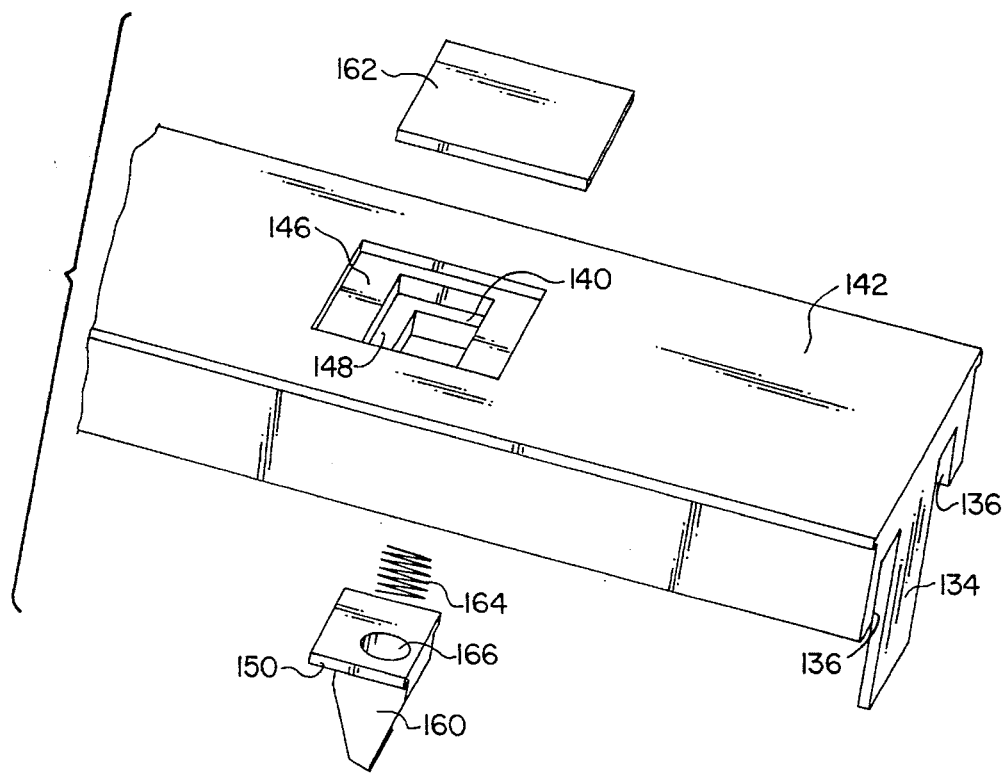
FIG. 18 is an enlarged, exploded view of portion B of FIG. 4.
Figure 19:
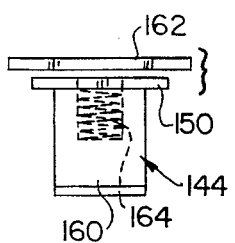
FIG. 19 is an enlarged, end view of the spring backstop of the present invention.

FIG. 4 and FIGS. 8 and 9 show the upper housing portion 104 of the housing assembly 23. The upper housing portion 104 is generally of rectangular shape with a top, front and two side walls. The front wall 134 includes two generally rectangular openings 136 therein allowing a suture element 60 to exit the device 10. With reference to FIG. 18, an opening 140 is defined in the top wall 142. A stop assembly, generally indicated at 144, is disposed in the opening 140. The opening 140 contains a first recessed shelf 146 and a second recessed shelf 148. The second shelf 148 receives a flange 150 of a spring backstop 160. The first shelf 146 receives a cover 162 which closes the opening 140. The cover 162 may be fixed by adhesive to the surface defining shelf 146. The second self 148 has enough depth to permit the spring backstop 160 to move upwardly enough to let a cross bar 163 of a suture element 60 move forwardly, as explained below. A spring 164 is accommodated within bore 166 such that it pushes through the top of backstop 160 and against the cover 162. As shown in FIG. 9, the underside of the upper housing portion 104 is contoured at 168 to push a forwardmost suture element downwardly as it moves forward. Further, a notch 170 is provided to allow the suture spring bar 38 to move to its most forward position to advance the forwardmost suture element. Side walls 172 and 174 are stepped at 176 so as to fit over the relief 120 of the lower housing portion 106.

Figure 11:
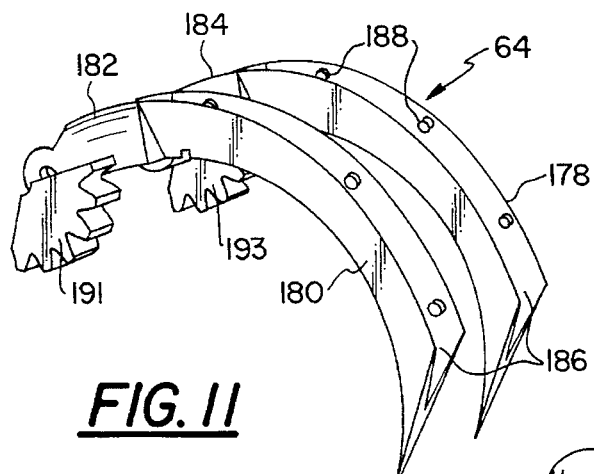
FIG. 11 is an enlarged, perspective view of the suture delivery structure provided in accordance with the present invention.
Figure 13:
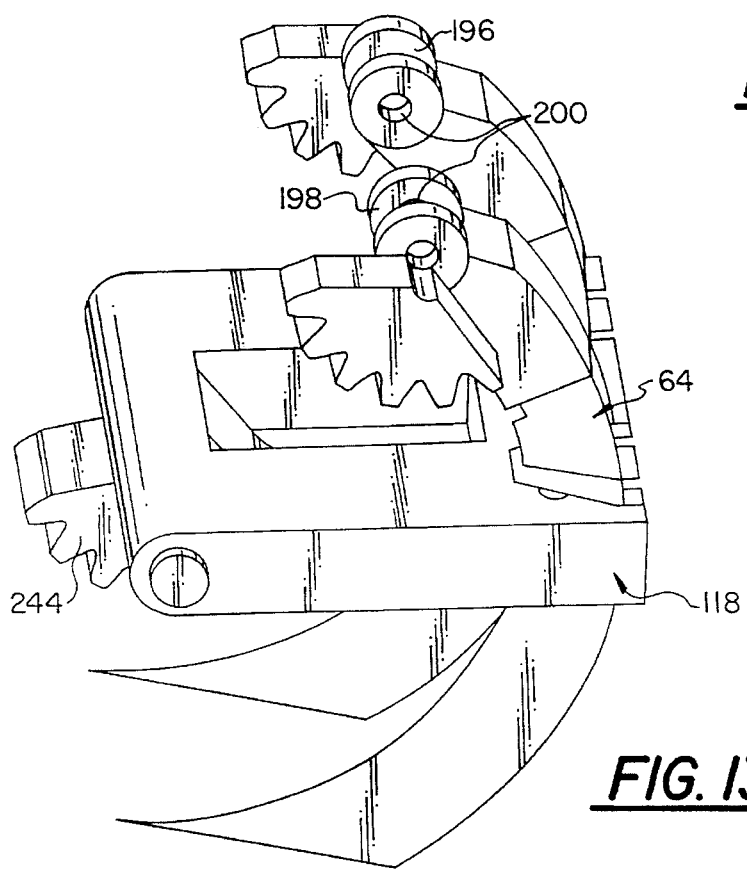
FIG. 13 is an enlarged, perspective view showing the suture delivery structure cooperating with the receptacle delivery structure.

As best shown in FIG. 4, the device 10 includes suture delivery structure, which, in the illustrated embodiment, is in the form of the suture needle 64 pivotally coupled to the second slide member 19. With reference to FIG. 11, the suture needle 64 is arcuate defined by a pair of spaced needle members 178, 180. Each needle member is defined by a 150° arc. The cross-section of each needle member is generally triangular and includes a rectangular portion 182, 184 at an end thereof. A generally V-shaped groove 186 runs longitudinally along the circumference of each needle member 178, 180 which is constructed and arranged to receive and hold a suture element 60. Protuberances 188 are provided along each side wall defining the grooves of each needle member 178, 180, and are arranged to engage a groove 189 provided in the suture element 60 so as to ensure that the suture element is held in a firm position in the needle members. Each needle member 178, 180 also includes a partial gear 191, 193 at its end which rotates the suture needle 64 when engaged with an associated flat gear 190, 192 of brace structure 194 (FIG. 20), as will be explained in greater detail below. As best shown in FIG. 13, each needle member 178, 180 includes a boss 196, 198 with bores 200 therethrough. As noted above, pins 66 extend through the bore 200 to couple the suture needle 64 to the distal end of the second slide member 19.

Figure 20:
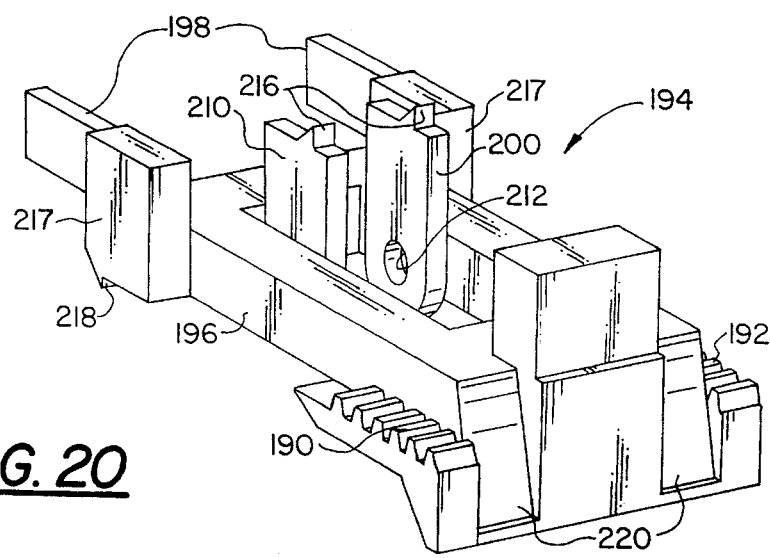
FIG. 20 is an enlarged, perspective view of the brace structure of the arm assembly.

FIG. 20 shows the brace structure 194 of the arm assembly 12. The brace structure 194 includes a body member 196, with a pair of tabs 198 extending longitudinally from the body member 196. The tabs 198 are constructed and arranged to be inserted into the notches 124 of the lower housing portion 106 as shown in FIG. 22, to secure the brace structure 194 to the lower housing portion 106. A pair of support posts 200, 210 extend upwardly from the body member 196. Each support 200, 210 includes a bore 212 therethrough which provides the attachment for a circular gear 214, rotatably coupled thereto. An upper portion of each support post 210 and 200 includes projections 216, which prevent succeeding suture elements of the series of suture elements from advancing as they are loaded. A rib portion 217 of the body member 196 includes a projection 218 on a lower surface thereof which prevents a succeeding receptacle element 86 from advancing until falling into its loading position.

As noted above, disposed on each side of the body member 196 are flat gears 190 and 192 which operate to rotate the suture needle 64. Disposed adjacent each flat gear is a well 220 which defines a resting support for a respective needle member 180 and 178 of the suture needle 64.

Figure 10:
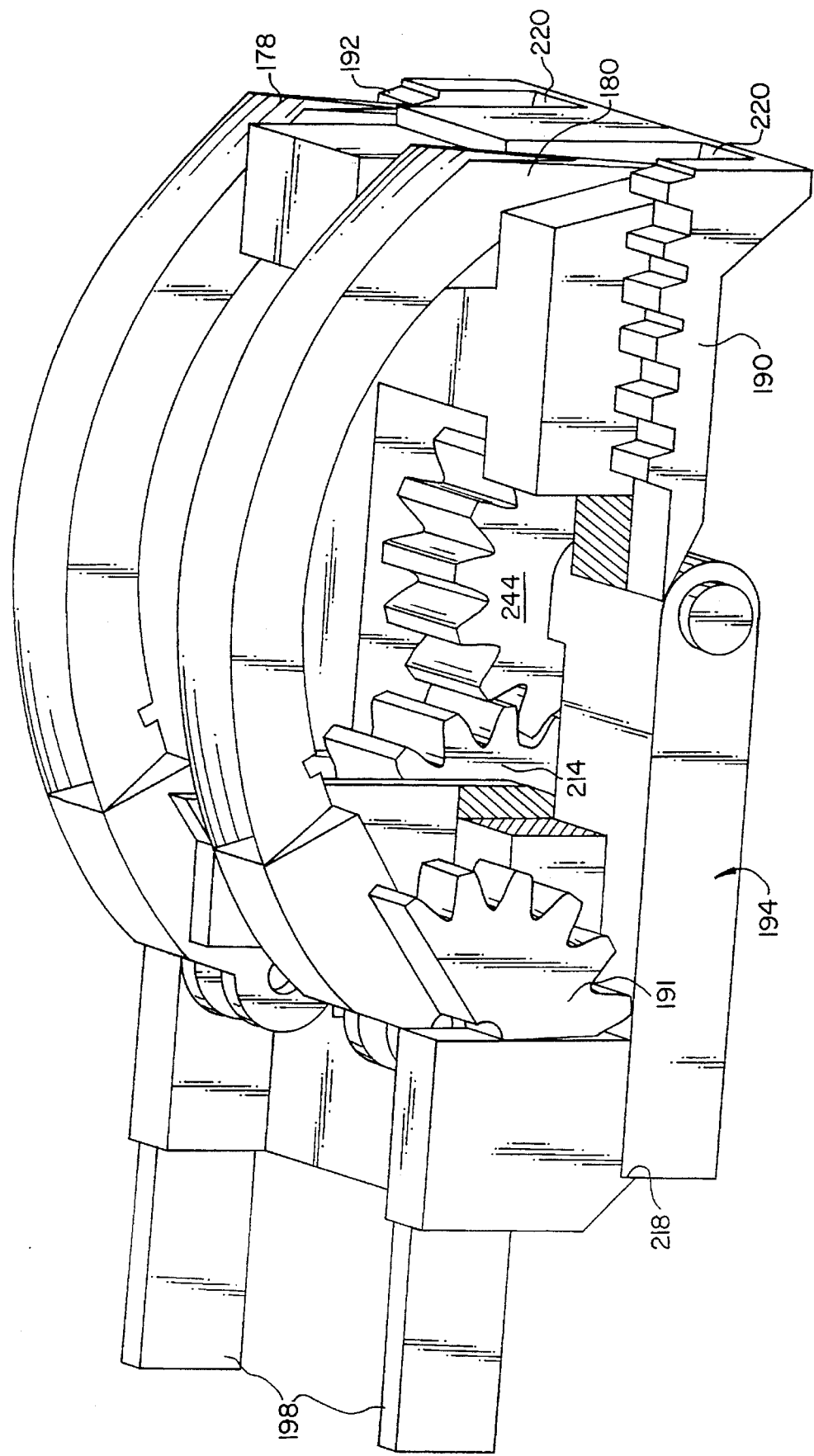
FIG. 10 is an enlarged, perspective view showing the relationship between suture delivery structure and a brace structure of the arm assembly.
Figure 12:
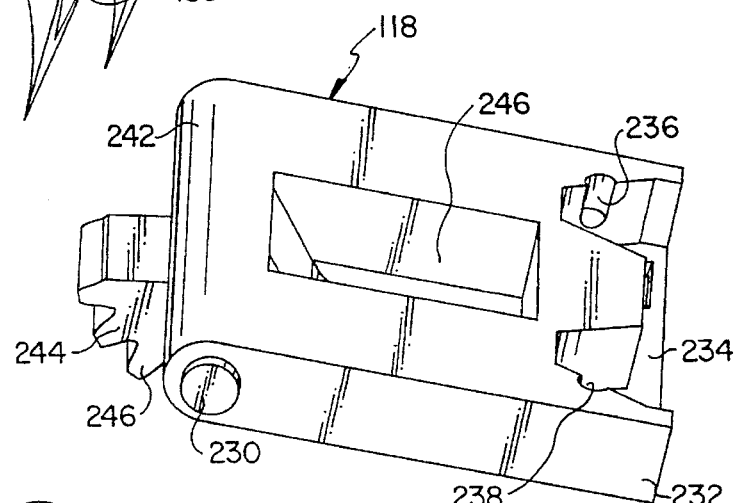
FIG. 12 is an enlarged, perspective view of the receptacle delivery structure provided in accordance with the present invention.

With reference to FIG. 4, the device 10 includes receptacle delivery structure, which, in the illustrated embodiment, is in the form of a receptacle arm 118, pivotally coupled to the distal portion of the lower housing portion 106. As shown in FIG. 12, the receptacle arm 118 includes a protrusion 230 on each side thereof. The protrusions 230 engage with bore 116 in the lower housing portion 106 to pivotally couple the receptacle arm 118 thereto. End 232 of the receptacle arm 118 includes a fossa 234 which corresponds to the shape of a receptacle element 86 so as to hold a receptacle element therein. The fossa 234 includes grooves 236, 238 which are constructed and arranged to receive an associated protuberance 240 (FIG. 16) of a receptacle element 86. End 240 of the receptacle arm 118 includes a partial gear 244, fixed thereto, including a plurality of teeth 246. The teeth of gear 244 cooperate with the teeth of gear 214 to permit the receptacle arm 118 to rotate from a loading position, shown in FIG. 10, to an unloading position shown in FIG. 7. It should be noted that in FIG. 7, the brace structure 194 is broken away to show the inter-engagement of two gears 214 and 244 clearly. A central portion of the receptacle arm 118 includes a cut-out 246 so as to accommodate gear 214 therein, when the receptacle arm 118 is in its loading position.

Figure 14:
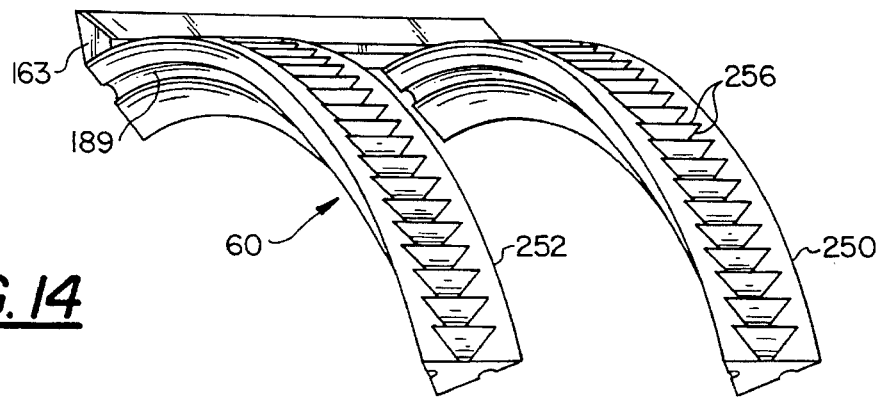
FIG. 14 is an enlarged, perspective view of a mechanical suture element provided in accordance with the invention.
Figure 15:
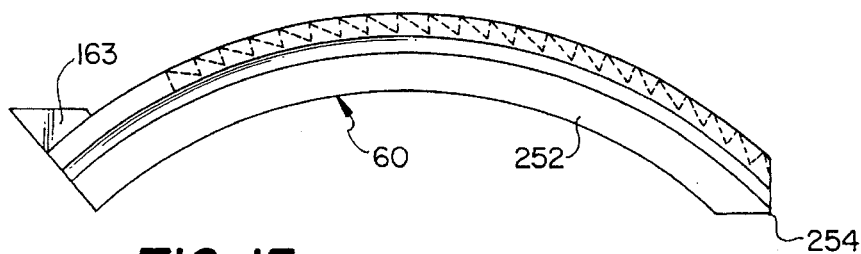
FIG. 15 is an enlarged, side view of the suture element of FIG. 14.

FIGS. 14 and 15 show the mechanical suture element 60, provided in accordance with the invention. The suture element 60 is preferably made of bioabsorbable material such as polydiazanone. In the illustrated embodiment, the suture element 60 includes two leg members 250, 252 which are curved so as to follow the contour of the curvature of the needle members 178, 180. The underside of each leg member 250, 252 includes a groove 189 which cooperates with the protuberances 188 of the V-shaped groove 186 of the associated needle member to ensure that the suture element 60 is held in position on the suture needle 64. The leg members, 250, 252 are coupled together via the cross bar 163. The cross bar 163 is constructed and arranged to cooperate with the stop assembly 144 of the upper housing portion 106 during delivery of a suture element, as will become apparent below. As shown in FIG. 5, the distal end of the suture element 60 terminates in a point 254 which aids in delivering the suture element 60 into tissue. An upper surface of each leg member 250, 252 includes a plurality of indentations 256 which cooperate with indentation engaging members 258 of a receptacle element 86 so as to define a ratchet-type mechanism for securing and tightening the suture element/receptacle element assembly against tissue.

Figure 16:
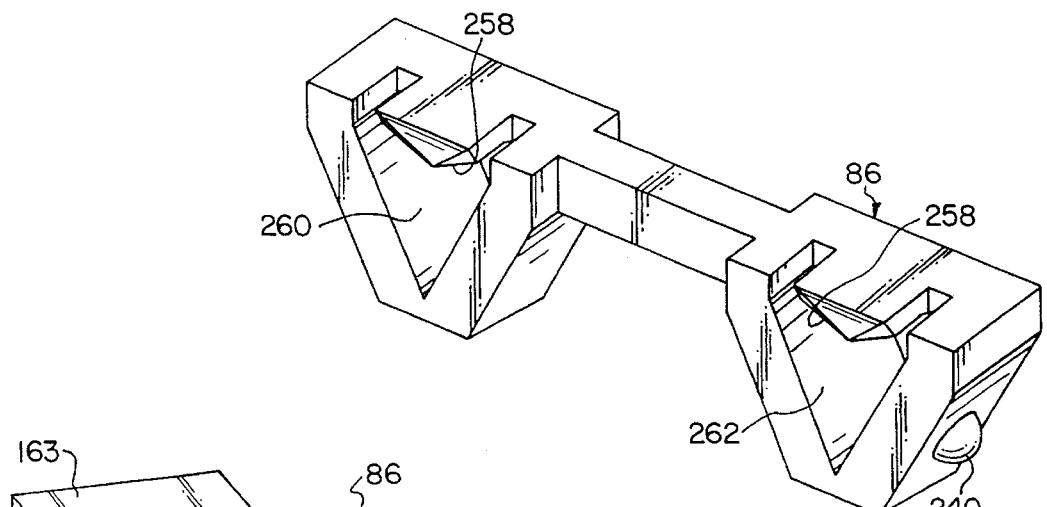
FIG. 16 is an enlarged, perspective view of a receptacle element provided in accordance with the invention.
Figure 17:
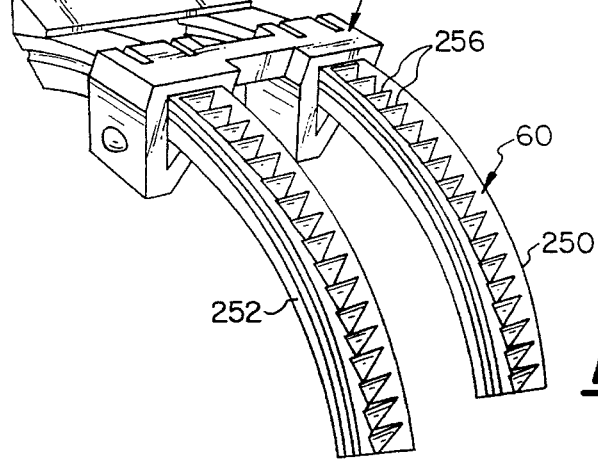
FIG. 17 is an enlarged, perspective view of a suture element secured to a receptacle element.

The receptacle element 86, shown in FIG. 16, is preferably made of the same bioabsorbable material as the suture element 60. Receptacle element 86 includes first and second spaced receiving channels 260, 262 for receiving an associated leg member 250, 252 of the suture element 60.

With reference to FIGS. 1A through 3B, the handle structure 16 is shown which includes a main body 263 having a finger grip member 264 and a thumb engaging member 266 disposed opposite to the grip member 264. The thumb engaging member 266 includes a pin 268 for pivotally coupling the thumb engaging member to the main body 263. A handle spring 270 is affixed to the pin 268 and biases the thumb engaging member 266 to its first, unactuated position (FIG. 1A). The thumb engaging member 266 also accommodates the lever 24 which is coupled to the first slide member 18 to initiate movement of the actuating structure 14. The finger grip member 264 is fixed to the main body 263. Thus, movement of the thumb engaging member 266 against the bias of the spring 270 to its second, actuated position (FIG. 1B) will move the actuating structure from its first position to its extended, or second position.

Figure 6A:
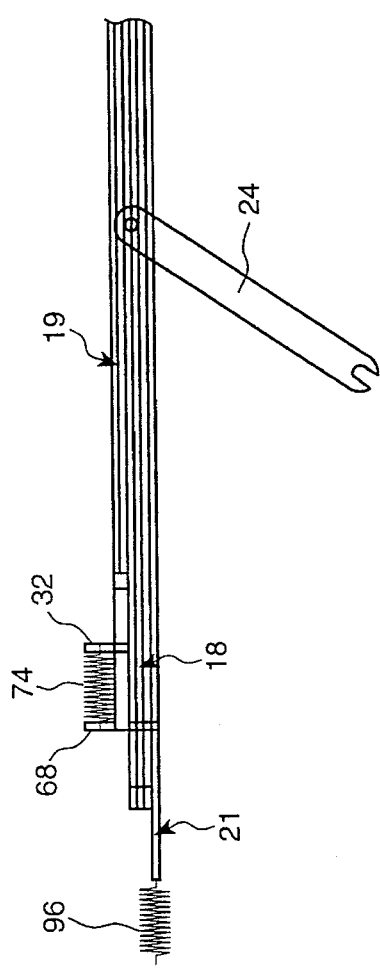
FIG. 6A is an enlarged, partial front view of the first slide member shown pulling the second slide member.
Figure 6B:
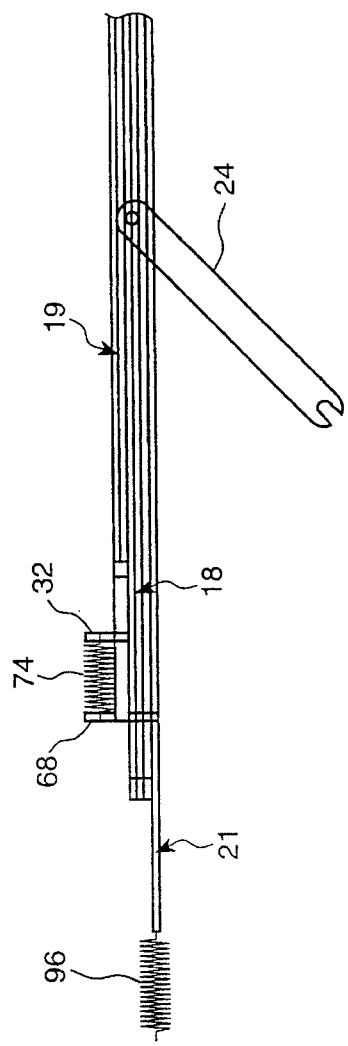
FIG. 6B is a view similar to FIG. 6A, showing the second slide member pushing the third slide member thereby stretching a spring.
Figure 6C:
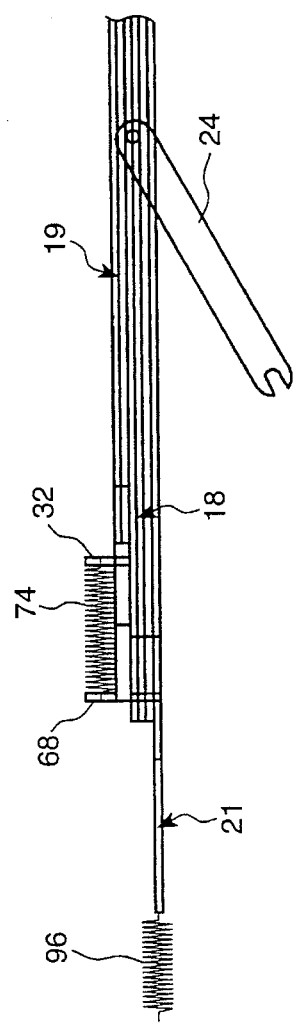
FIG. 6C is a view similar to FIG. 6B, showing the first slide member moved forwardly while the second and third slide members remain at rest.

As shown in FIGS. 2A and 2B, the actuating structure 14, when assembled, includes the first, second and third slide members, and engagement structure, in the form of gears 190–193, 214 and 244. The first slide member 18 is disposed between the third and second slide members, 21 and 19, respectively. Thus, when the handle structure 16 is moved from its first position (FIG. 1A) to its second position (FIG. 1B) by moving engaging member 266 to its actuated position, the first slide member 18 is moved forwardly. Since the first slide member 18 is coupled to the second slide member 19 by the spring 74, and the second slide member 19 is coupled to the third slide member 21, all three slide members move together. FIGS. 6A through 6C show schematically the relative movement of the slide members 18, 19 and 21 upon actuation of the handle structure 16. As shown in FIG. 6A, the first slide member 18 pulls the second slide member 19 stretching the relatively stiff spring 74. FIG. 6B shows the second slide member 19 pushing the third slide member 21 while stretching the spring 96. Spring 96 is more resilient than spring 74. FIG. 6C shows the second slide member 19 and third slide member 21 at rest as the first slide member 18 moves further to its extended position.

Thus, actuation of the thumb engaging member 266 advances the three slide members forward on a compression cycle and backward on a retraction cycle. The result, through the action of the gears or engagement structure, is a clockwise rotation of the suture needle 64 and a counterclockwise rotation of the receptacle arm 118, as discussed in further detail below.

Figure 23A:
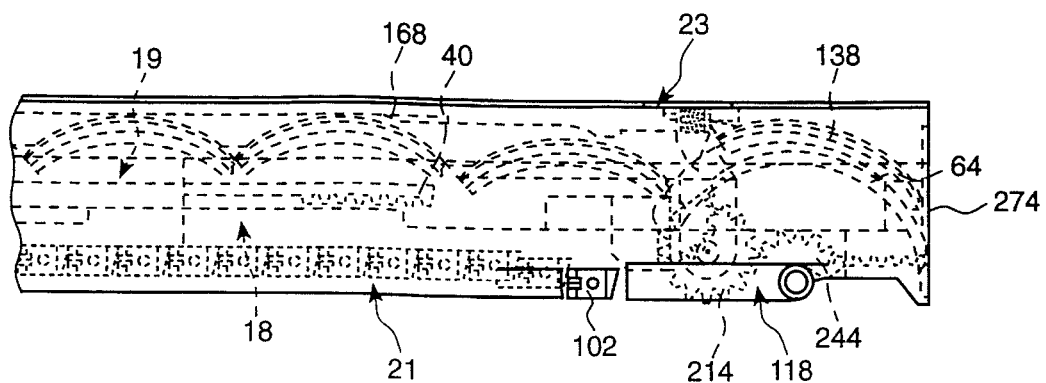
FIGS. 23A through 23J show the sequential operation of the arm assembly delivering a forwardmost suture element and receptacle element and loading a successive suture element and receptacle element.

A suture element delivery cycle includes a suture element and receptacle element discharge phase and suture element and receptacle element return or loading phase. The suture element and receptacle element discharge phase is shown schematically in FIGS. 23A through 23D. When the thumb engaging member 266 of the handle structure 16 is in its unactuated position as shown in FIG. 1A, the suture needle 64 is in its completely retracted position, as shown in FIG. 23A. A forwardmost suture element 138 is sitting loosely in the grooves 186 of the suture needle 64 waiting to be snapped firmly into position therein as it brushes the top of the upper housing portion 104 as it exits through the distal opening 274 in the housing assembly 23. The forwardmost receptacle element 102 is resting on the floor (not shown) of the lower housing portion 106, waiting to be pushed into the empty receptacle fossa 234 by the third slide member 21. The lower housing portion is not shown in FIGS. 23A–23J for clarity of illustration. The first slide member 18 is shown in its first, or initial position. At the distal end of the device 10, two gears are engaged. The first gear is the circular gear 214 which will engage and turn the partial gear 244 on the receptacle arm 118 to rotate the receptacle arm 118 counterclockwise.

Figure 23B:
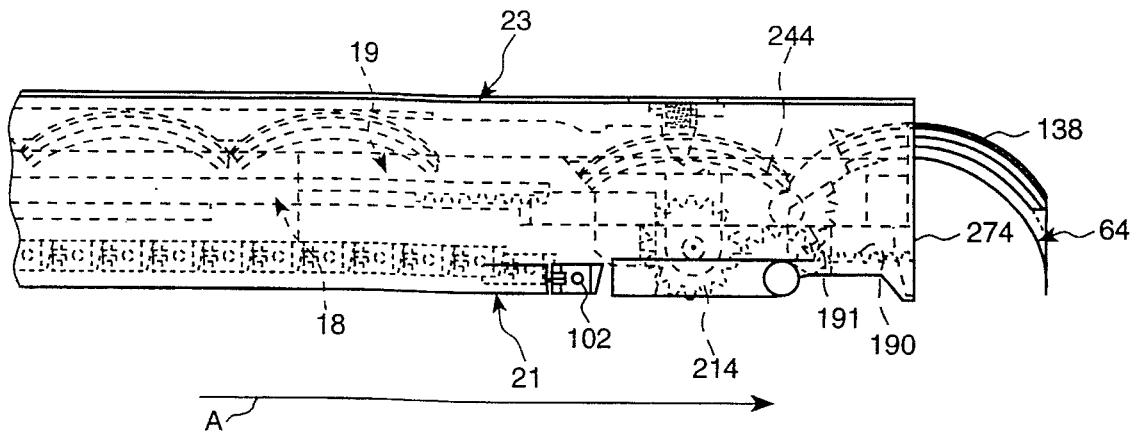

FIG. 23B shows the initial change of position of the slide members upon movement of the thumb-engaging engaging portion to its actuated position, which in turn advances the actuating structure 14 and thus, the suture needle 64. Thus, the second slide member 19 is pulled forward in the direction of arrow A by the first slide member 18, as explained above. The first slide member 18 has not yet reached its target gear 214.

Figure 7:
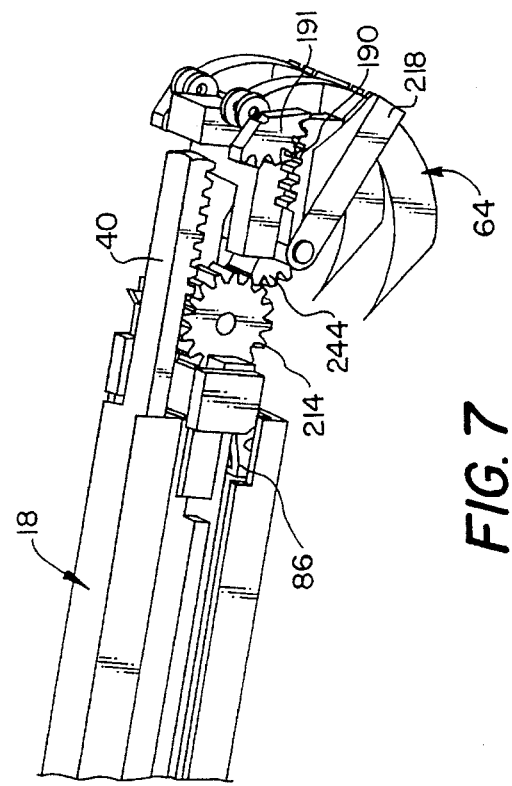
FIG. 7 is an enlarged, partial perspective view of the distal end of the arm assembly showing the suture delivery structure and the receptacle delivery structure coupled thereto.
Figure 23C:
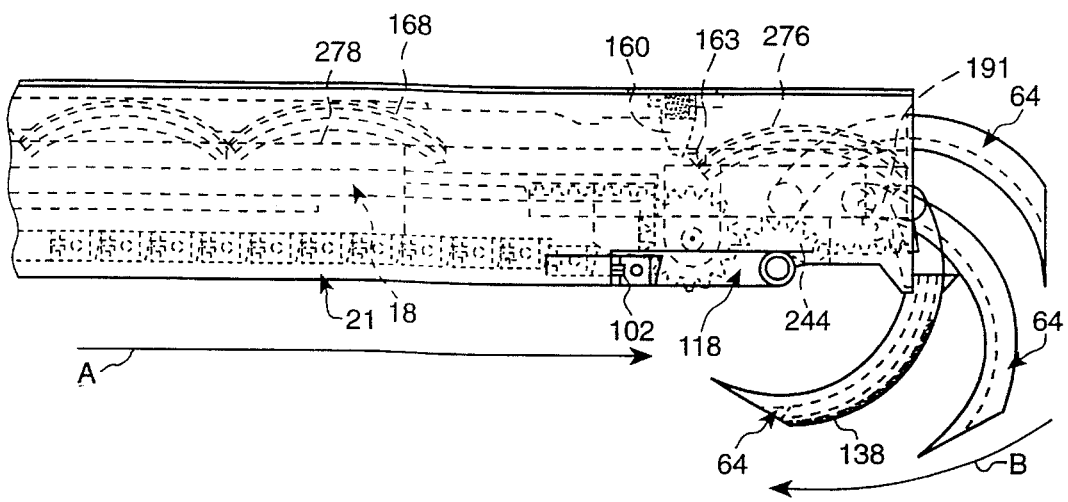

FIG. 23C demonstrates the rotation of the suture needle 64 at various extended positions due to cooperation of the engagement structure which is in the form of gears 190 to 193. Thus, the suture needle 64 rotates as its partial gears 191, 193 move forwardly over the flat or elongate gears 190, 192 (FIG. 7). The first slide member 18 has not yet reached the circular gear 214. The third slide member 21 has completed its total forward motion pushing the leading receptacle element 102 into the fossa 234 of the receptacle arm 118 and completes this motion generally simultaneously as the suture needle 64 reaches its final, downward position by being rotated clockwise in the direction of arrow B. The succeeding suture element 276 has passed under the spring backstop 160 and is ready to be loaded during the loading cycle phase. The remaining suture elements are held further back by the contour of the upper housing portion 104 and the higher level portion 270 (FIG. 4) of the second slide member 19.

Figure 23D:
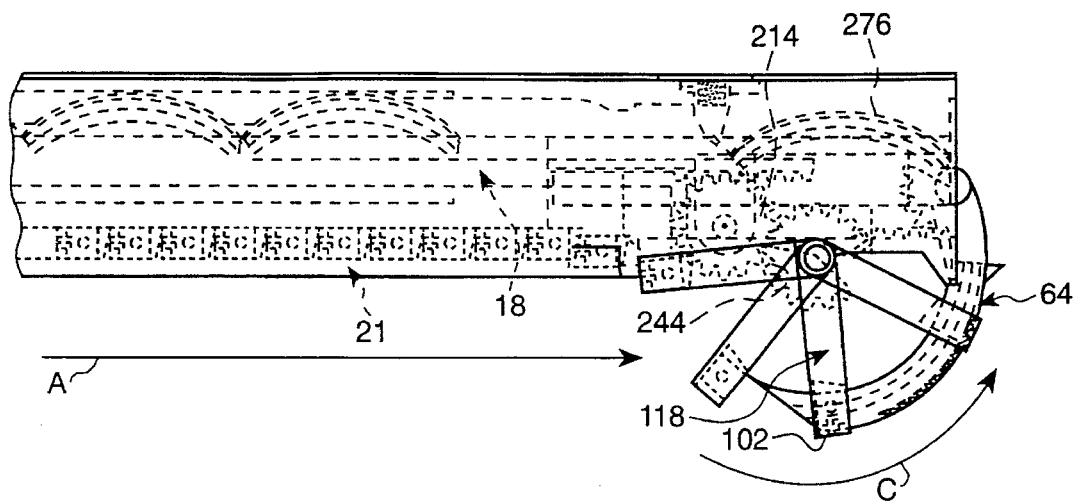

FIG. 23D shows the progression of movement of the first slide member 18 to its final position due to the cooperation of the engagement structure which is in the form of gears 40, 214 and 244. Gear 40 engages the circular gear 214 which in turn engages partial gear 244 to rotate the receptacle arm 118 in the direction of arrow C. This action can only occur when the suture needle 64 is in its downward position because the receptacle arm 118 must pivot around the center of a circle congruent to the arc of the suture needle 64. In this position, the forwardmost receptacle element 102 can slide smoothly over the needles 178, 180 of the suture needle 64.

Figure 23E:
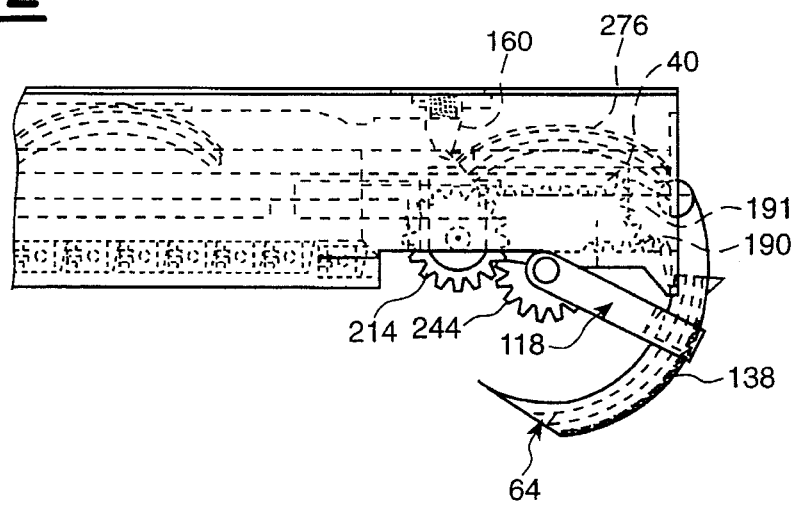

FIG. 23E shows the most extreme position of the receptacle arm 118 and marks the end of the discharge phase of the suture element cycle. The final or most extreme position of the receptacle arm (FIG. 23D) is optional and dependent upon tissue thickness. The thickness of tissue to be sutured can range from 6.5 mm, limited by the length of a suture element 60 which, in the illustrated embodiment, is 2.5 mm.

Figure 23F:
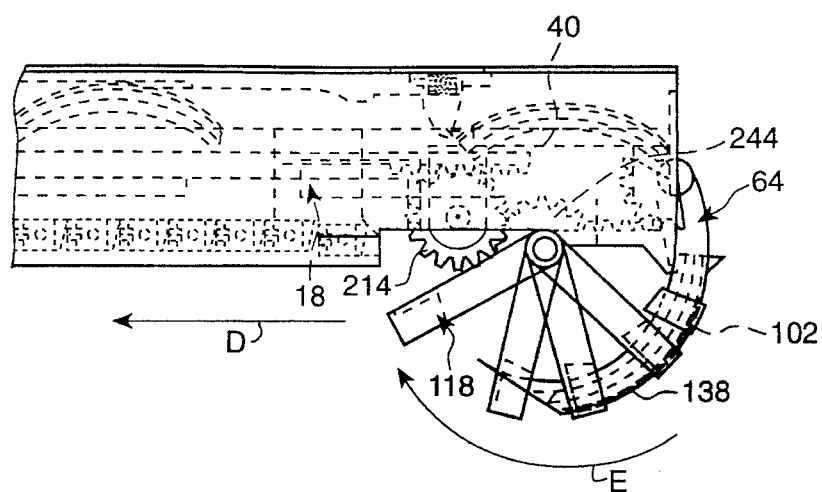

FIG. 23F shows the first action of the actuating structure 14 upon release of the handle structure 16. As the force on the handle structure 16 is released such that spring 270 returns the handle structure to its first position thereof, the first slide member 18 retracts in the direction of arrow D with gear 40 moving circular gear 214 which in turn rotates gear 244 to move the receptacle arm 118 in the direction of arrow E thus, returning the receptacle arm 118 to its loading position. The receptacle element 102 has slid out of its fossa 234 and is held and locked to the suture element 130 due to the inter-engaging ratchet mechanism.

Figure 23G:
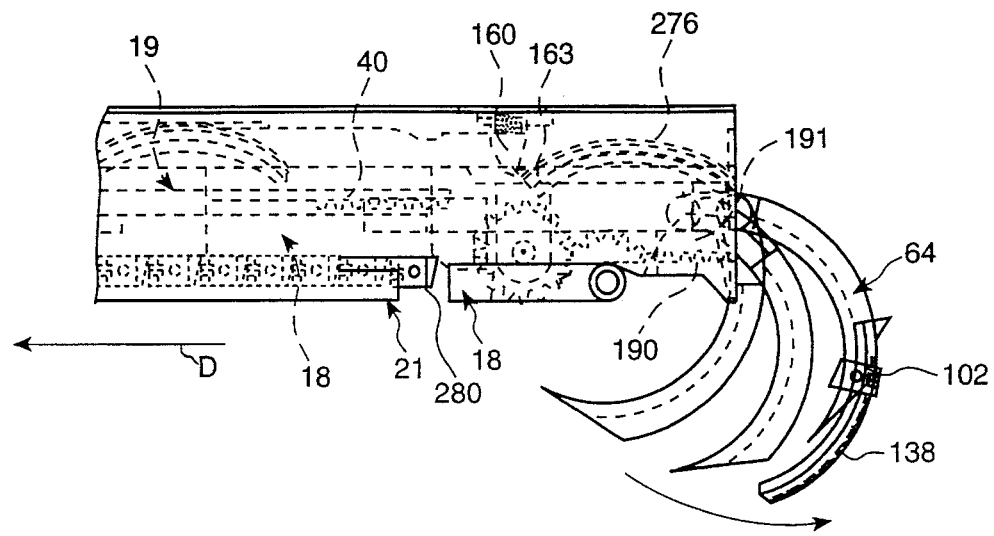

FIG. 23G shows the retraction of the second slide member 19 and the third slide member 21 which are pulled by the first slide member 18. This begins the loading action of the succeeding suture element 276. The posterior part of the succeeding suture element 276 is held in place by the spring backstop 160 engaging the cross bar 163 of the suture element 276. Suture element 276 is prevented from moving forward by the projections 216 of the brace structure 194 until the suture element 276 has been lifted over the brace structure 194. As shown in FIG. 23G, the discharged suture element is sliding out of the anterior end of the suture needle 64. The posterior end of the empty suture needle is entering the housing assembly 23 and beginning to lift the anterior end of the succeeding suture element 276. FIG. 23G also shows the third slide member 21 retracting and simultaneously depositing the succeeding receptacle element 280 on the floor of the lower housing portion 106 (not shown).

Figure 23H:
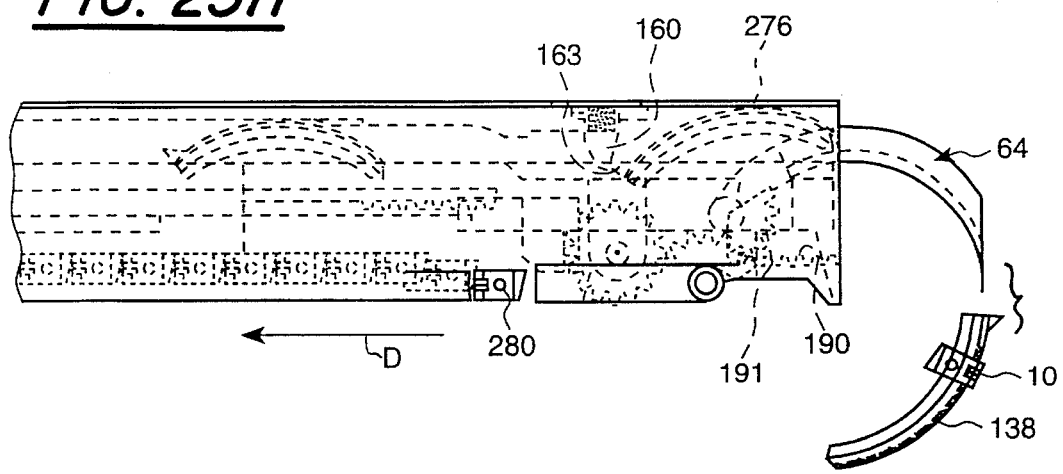

FIG. 23H shows the succeeding suture element 276 in its loading position. The succeeding suture element 276 is continuing to slide-up the empty suture needle 64 while it is still braced posteriorly against the spring backstop 160. As shown, the receptacle element 102 is engaged with the suture element 138 remote from the device 10.

Figure 23I:
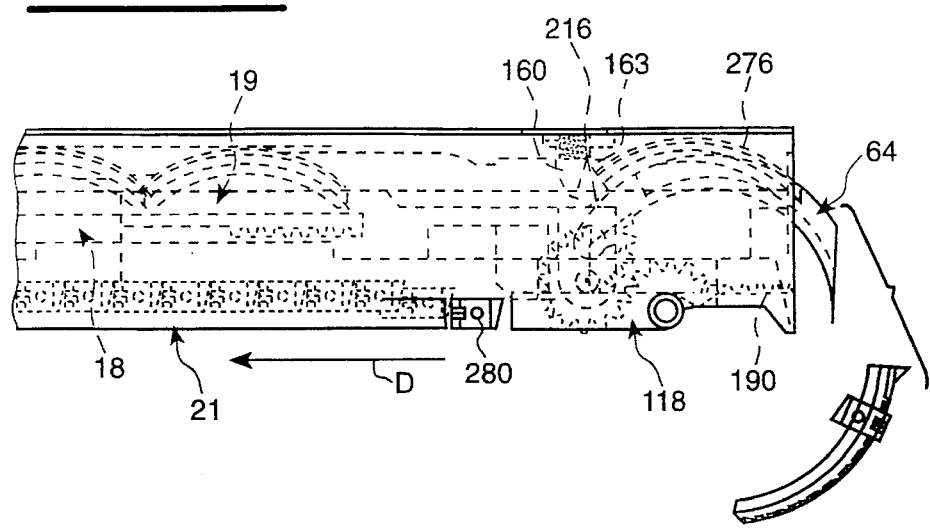

FIG. 23I demonstrates the migration of the posterior end of the succeeding suture element 276 sliding upwardly along the spring backstop 160. It should be noted that the backstop 160 is medial to the suture needle, contacting only the cross bar 163 of the suture element 276.

Figure 23J:
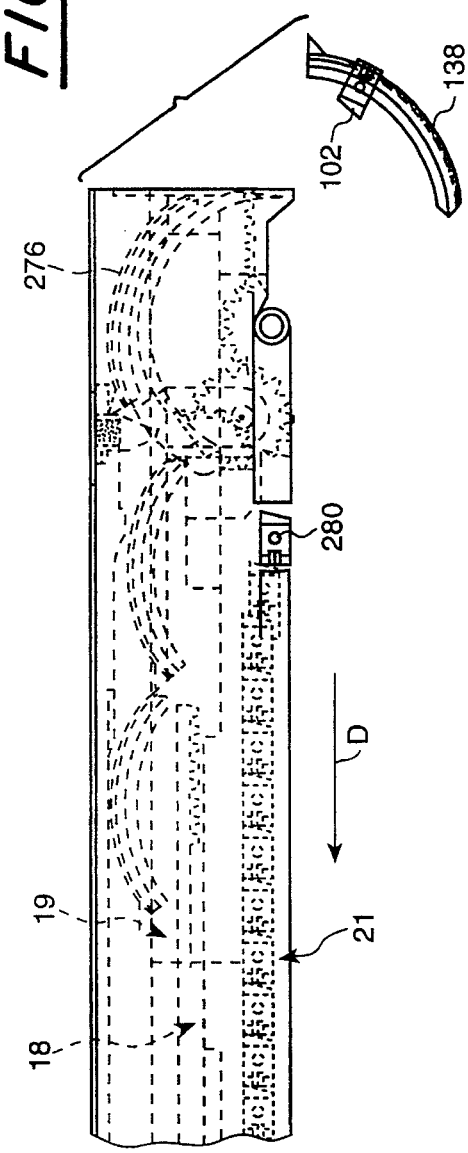

FIG. 23J is the new, ready position of the succeeding suture element 276 which is now is the forwardmost suture element at the end of the suture cycle.

Figure 24:
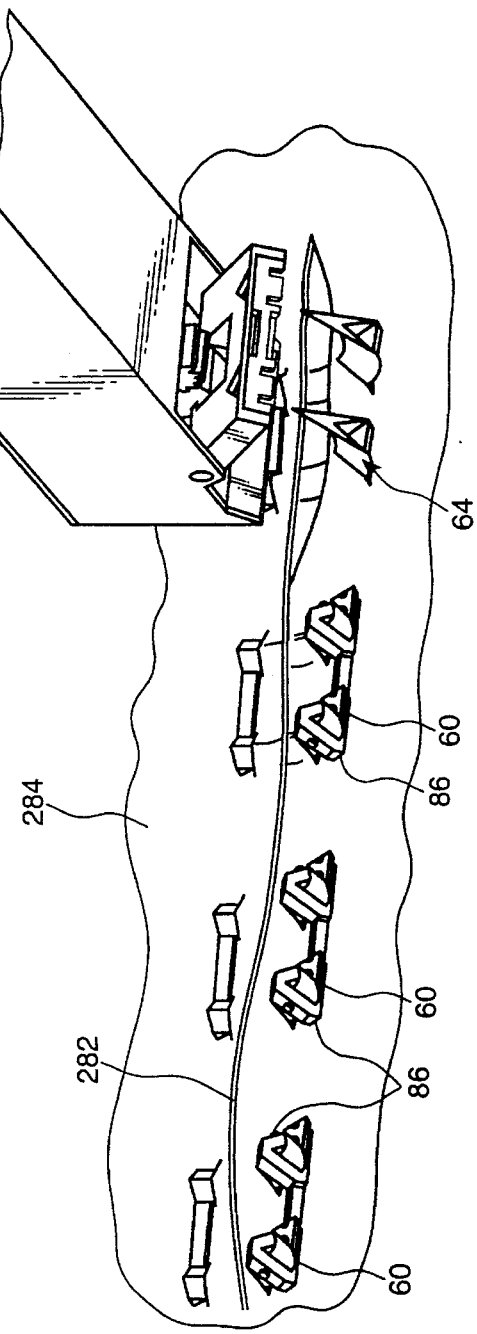
FIG. 24 is an enlarged, perspective view showing the device of the invention delivering a series of suture elements and receptacle elements to fasten tissue.

FIG. 24 shows the device 10 with its arm assembly 12 thereof moved to a suture delivery location, delivering a series of suture elements 60 and receptacle elements 86 to close an incision 282 in tissue 284.

In the illustrated embodiment, the arm assembly 12 is rectangular having a height H of approximately 8.75 mm and a width W of approximately 8.50 mm, which allows more than enough tolerance for use with conventional 10 mm trocars employed in laparoscopic surgery. The arm assembly 12 is about 29 cm in length which can be modified easily depending on use and the number of suture elements desired.

It is within the contemplation of the invention to employ the device in general surgery, orthopedics, and OB-GYN procedures. For example, the device 10 may be used to suture bowel and soft tissues, such as liver tissue, following a biopsy. Arthroscopic repair of ligaments could be made easily with the device 10. The device 10 can be sized down to less than 5 mm to permit entry into shoulder and knee joints.

It can be seen that the device 10 of the present invention provides an effective means of delivering and securing a suture element in tissue, particularly, endoscopically. The ability to deliver a series of suture elements with only one hand advantageously permits the surgeon to utilize his other hand, if necessary.

Although in the illustrated embodiment the suture needle 64 and receptacle arm are rotated via the engagement structure in the form of particular gears, it is within the contemplation of the invention to provide any one of a variety of controlled displacement mechanisms to perform the rotation function.

It thus will be seen that the objects of this invention have been fully and effectively accomplished. It will be realized, however, that the foregoing preferred embodiment of the present invention has been shown and described for the purpose of illustrating the structural and functional principles of the present invention and is subject to change without departure from such principles. Therefore, this invention includes all modifications accomplished within the spirit of the following claims.

What is claimed is:

1. A suture element delivery device comprising:

an elongated arm assembly including a housing assembly having proximal and distal ends;

a series of successive suture elements carried by said arm assembly;

suture delivery structure mounted to said housing assembly for movement between a retracted position disposed within said housing assembly and an extended position extending distally from said housing assembly, said suture delivery structure being constructed and arranged to engage and displace a forwardmost suture element;

receptacle delivery structure mounted to a distal end of said housing assembly and movable between receptacle loading and unloading positions, said receptacle delivery structure being constructed and arranged to engage and displace a forwardmost receptacle element;

actuating structure carried by said arm assembly constructed and arranged to move said suture delivery structure between its retracted and extended positions and said receptacle delivery structure between its loading and unloading positions; and handle structure coupled to said proximal end of said arm assembly and operatively coupled to said actuating structure, said handle structure being movable between first and second positions such that movement of said handle structure from said first position to said second position thereof during a suturing operation moves said actuating structure between first and second positions, thereby moving said suture delivery structure from its retracted position to its extended position and moving said receptacle delivery structure with a forwardmost receptacle element therein from its loading position to its unloading position such that a forwardmost suture element and the associated forwardmost receptacle element are displaced from the distal end of said housing assembly and into engagement, and movement of said handle structure from said second position to said first position thereof returns said actuating structure to its first position thereby moving said suture delivery structure from said extended position to said retracted position and moving said receptacle delivery structure from said unloading position to said loading position.

2. The device according to claim 1, wherein said actuating structure includes at least one slide member movable along a longitudinal axis of said arm assembly upon movement of said handle structure for moving said suture delivery structure between its retracted and extended positions and said receptacle delivery structure between its loading and unloading positions.

3. The device according to claim 1, wherein said actuating structure includes:

a first slide member having proximal and distal ends, said proximal end being coupled to said handle structure so that said first slide member is movable between first and second positions upon movement of said handle structure between the first and second positions of said handle structure;

a second slide member operatively coupled to said first slide member and selectively movable therewith between first and second positions, said second slide member having proximal and distal ends, said suture delivery structure being pivotally coupled to the distal end of said second slide member;

a third slide member operatively coupled to said second slide member and movable therewith between first and second positions, said third slide member having proximal and distal ends, said proximal end thereof being coupled to said housing structure, said distal end being constructed and arranged to receive a forwardmost receptacle element; and engagement structure operatively coupled to said suture delivery structure and to said receptacle delivery structure and constructed and arranged to move said suture delivery structure between its retracted and extended positions and said receptacle delivery structure between its loading and unloading positions, said series of successive suture elements being carried by said second slide member, said series of successive receptacle elements being carried by said third slide member, whereby movement of said handle structure to its second position moves said first slide member from its first position to its second position, said first slide member moving said second slide member from its first position to its second position thereby operating said engagement structure to move said suture delivery structure, with a forwardmost suture element engaged therewith, from its retracted position to its extended position, said second slide member in turn moving said third slide member between its first and second positions thereby operating said engagement structure to move said receptacle delivery structure, with a forwardmost receptacle element engaged therewith, from its loading position to its unloading position such that the forwardmost suture element engages the forwardmost receptacle element, release of said handle structure returning said first, second, and third slide members to their respective first positions, said receptacle delivery structure to its loading position in position to receive the succeeding receptacle element of the series of receptacle elements, and said suture delivery structure to its retraced position thereby engaging the succeeding suture element of the series of successive suture elements.

4. The device according to claim 3, wherein said arm assembly further includes brace structure fixed to said distal end of said housing assembly constructed and arranged to support said suture delivery structure when in said retracted position thereof.

5. The device according to claim 4, wherein said arm assembly includes biasing structure constructed and arranged to bias said series of successive receptacle elements and said series of successive suture elements towards said distal end of said arm assembly.

6. The device according to claim 5, wherein said biasing structure comprises first and second assemblies carried within said housing assembly, said first assembly biasing said suture elements and said second assembly biasing said receptacle elements.

7. The device according to claim 4, wherein said handle structure includes a stationary finger grip portion and a movable thumb-engaging portion disposed opposite thereto, said thumb-engaging portion being coupled to said first slide member and movable between unactuated and actuated positions such that movement of said thumb-engaging portion between its unactuated and actuated positions moves said first slide member between its first and second positions.

8. The device according to claim 4, wherein said engagement structure comprises:

elongate gears defined at a distal end of said brace structure and partial circular gears defined on said suture delivery structure, said partial circular gears engaging said elongate gears as said second slide member moves between its first and second positions to pivot said suture delivery structure between its retracted and its extended positions; and an elongate gear coupled to a distal end of said first slide member, a partial circular gear coupled to said receptacle delivery structure and a circular gear coupled to said brace structure so as to be rotatable with respect thereto, said elongate gear engaging said circular gear as said first slide member moves between its first and second positions while said circular gear engages said partial gear of said receptacle delivery structure to pivot said receptacle delivery structure between its loading and unloading positions.

9. The device according to claim 8, wherein said suture delivery device comprises a suture needle having first and second spaced needle members of arcuate configuration, each needle member being pivotally coupled to said distal end of said second slide member and including a respective said partial circular gear, each said needle member including a generally V-shaped groove therein constructed and arranged to receive a suture element therein, each suture element of said series of suture elements having first and second spaced leg members coupled together at an end thereof by a cross bar member, said leg members being of arcuate shape so as to correspond to a shape of said needle members and being constructed and arranged to be received in a groove of an associated needle member such that said suture element may move with said suture needle as said suture needle moves from its retracted to its extended position, said suture needle cooperating with a successive suture element as said suture needle returns to its retracted position thereby placing said successive suture element in said grooves and in position to be moved with said suture needle as said suture needle moves to its extended position.

10. The device according to claim 8, wherein said receptacle delivery structure comprises a receptacle arm having a fossa in an end thereof which corresponds to a shape of a receptacle element so as to hold the forwardmost receptacle element therein such that said forwardmost receptacle may move with said receptacle arm as said receptacle arm moves from its loading position to its unloading position.

11. The device according to claim 1, wherein said handle structure includes a stationary finger grip portion and a movable thumb-engaging portion disposed opposite thereto, said thumb-engaging portion being operatively coupled with said actuating structure and movable between unactuated and actuated positions such that movement of said thumb-engaging portion between its unactuated and actuated positions moves said actuating structure between its first and second positions.

12. The device according to claim 1, wherein each suture element of said series of suture elements is bioabsorbable and has first and second spaced leg members coupled together at an end thereof by a cross bar member, each leg member being of arcuate shape and having a plurality of indentations in a surface thereof.

13. The device according to claim 12, wherein each receptacle element of said series of receptacle elements is bioabsorbable and has first and second spaced receiving channels for receiving an associated leg member of a suture element, each said channel including an indentation engaging member cooperable with said indentations so as to secure a suture element with respect to a receptacle element.

14. The device according to claim 13, wherein said bioabsorbable material is polydioxonone.

15. The device according to claim 1, wherein said arm assembly is generally rectangular having a height of less than or equal to approximately 8.75 mm and a width of less than or equal to approximately 8.50 mm.

16. A method of delivering a suture element endoscopically with a suture element delivery device, the device including an elongated arm assembly including a housing assembly having proximal and distal ends, a series of successive suture elements carried by the arm assembly, a series of successive receptacle elements carried by the arm assembly, suture delivery structure mounted to the housing assembly for movement between a retracted position disposed within said housing assembly and an extended position extending distally from the housing assembly, the suture delivery structure being constructed and arranged to engage and displace a forwardmost suture element, receptacle delivery structure mounted to a distal end of the housing assembly and movable between receptacle loading and unloading positions, the receptacle delivery structure being constructed and arranged to engage and displace a forwardmost receptacle element, actuating structure carried by the arm assembly constructed and arranged to move the suture delivery structure between its retracted and extended positions and the receptacle delivery structure between its loading and unloading positions, and handle structure coupled to the proximal end of the arm assembly and operatively coupled to the actuating structure, the handle structure being movable between first and second positions, the method including:

(a) moving the device such that the arm assembly thereof is disposed at a suture delivery location, (b) moving said handle structure from said first position to said second position thereof during a suturing operation thereby moving said actuating structure between first and second positions so as to move said suture delivery structure from its retracted position to its extended position and move said receptacle delivery structure from its loading position to its unloading position such that a forwardmost suture element and an associated forwardmost receptacle element are displaced from the distal end of said housing assembly into tissue with said suture element engaging said receptacle element, and (c) releasing said handle structure from its second position so as to return said actuating structure to its first position thereby moving said suture delivery structure from its extended position to its retracted position and moving said receptacle delivery structure from its unloading position to its loading position.

17. The method according to claim 16, further comprising incrementally advancing the device along tissue to be sutured and repeating steps (b) and (c) after each incremental advancement.

18. A suture element delivery device comprising:

an elongated arm assembly including a housing assembly having proximal and distal ends;

a series of successive suture elements carried by said arm assembly;

a series of successive receptacle elements carried by said arm assembly;

suture delivery structure mounted to said housing assembly for movement between a retracted position disposed within said housing assembly and an extended position extending from said housing assembly, said suture delivery structure being constructed and arranged to engage and displace a forwardmost suture element;

receptacle delivery structure mounted to a distal end of said housing assembly and movable between receptacle loading and unloading positions, said receptacle delivery structure being constructed and arranged to engage and displace a forwardmost receptacle element;

actuating structure carried by said arm assembly constructed and arranged to move said suture delivery structure between its retracted and extended positions and said receptacle delivery structure between its loading and unloading positions; and handle structure coupled to said proximal end of said arm assembly and operatively coupled to said actuating structure, said handle structure being movable between first and second positions such that movement of said handle structure from said first position to said second position thereof during a suturing operation moves said actuating structure between first and second positions, thereby moving said suture delivery structure from its retracted position to its extended position and moving said receptacle delivery structure from its loading position to its unloading position such that a forwardmost suture element and an associated forwardmost receptacle element are displaced from the distal end of said housing assembly and into engagement, and movement of said handle structure from said second position to said first position thereof returns said actuating structure to its first position thereby moving said suture delivery structure from said extended position to said retracted position and moving said receptacle delivery structure from said unloading position to said loading position, wherein each suture element of said series of suture elements is bioabsorbable and has first and second spaced leg members coupled together at an end thereof by a cross bar member, each leg member being of arcuate shape and having a plurality of indentations in a surface thereof.

\* \* \* \* \*